(12) United States Patent
Vogel et al.

(10) Patent No.: US 7,102,006 B2
(45) Date of Patent: Sep. 5, 2006

(54) PREPARATION OF METAL COMPLEXES

(75) Inventors: Alexander Vogel, Munich (DE); Edmund M. Carnahan, Fresno, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/524,331

(22) PCT Filed: Aug. 13, 2003

(86) PCT No.: PCT/US03/25228

§ 371 (c)(1),
(2), (4) Date: Feb. 11, 2005

(87) PCT Pub. No.: WO2004/024740

PCT Pub. Date: Mar. 25, 2004

(65) Prior Publication Data

US 2005/0222443 A1    Oct. 6, 2005

Related U.S. Application Data

(60) Provisional application No. 60/410,611, filed on Sep. 12, 2002.

(51) Int. Cl.
*C07F 7/00* (2006.01)
*B01J 31/00* (2006.01)

(52) U.S. Cl. ............... 546/2; 556/51; 502/155; 502/162

(58) Field of Classification Search ............ 546/2; 556/51; 502/155, 162
See application file for complete search history.

(56) References Cited

U.S. PATENT DOCUMENTS

| | | | |
|---|---|---|---|
| 5,312,938 A | 5/1994 | Hefner et al. | |
| 5,597,935 A | 1/1997 | Jordan et al. | |
| 5,861,352 A | 1/1999 | Gila et al. | |
| 5,880,302 A | 3/1999 | Herrmann et al. | |
| 6,020,444 A | 2/2000 | Riedel et al. | |
| 6,232,256 B1 | 5/2001 | Yang et al. | |
| 2005/0209472 A1* | 9/2005 | Vogel | 556/51 |

FOREIGN PATENT DOCUMENTS

WO    WO02/38628    5/2002

* cited by examiner

*Primary Examiner*—Porfirio Nazario-Gonzalez

(57) ABSTRACT

A process for the preparation of Group 4 metal hydrocarbyl complex the steps of the process comprising contacting a Group 4 metal amide with a neutral source of a monovalent or divalent, Lewis base ligand group and a Lewis acid hydrocarbylating agent under conditions to form a Group 4 metal hydrocarbyl complex.

14 Claims, No Drawings

PREPARATION OF METAL COMPLEXES

CROSS REFERENCE STATEMENT

This application claims the benefit of U.S. Provisional Application No. 60/410,611, filed Sep. 12, 2002.

BACKGROUND OF THE INVENTION

This invention relates generally to the preparation of certain Group 4 metal complexes by means of a combination amine elimination/alkylation process to produce metal complexes. More particularly the present invention relates to a novel process for conversion of initial Group 4 metal amides to the corresponding metal alkyl complexes.

The manufacture of Group 4 metal amide derivatives and subsequent conversion to the corresponding halide or alkyl metal complexes has been previously taught in U.S. Pat. Nos. 5,312,938, 5,597,935, 5,861,352, 5,880,302, 6,020,444, and 6,232,256, and elsewhere. In WO02/38628 Group 4 metal complexes containing "spectator ligands" such as amino-substituted cyclic amine compounds were prepared through a two step amine elimination/alkylation process. Suitable amide complexes for use in such process include Group 4 metal tetra(N,N-dialkylamido) compounds, especially titanium-, zirconium- or hafnium-tetrakis(N,N-dimethylamide) compounds. Suitable alkylating agents include trialkylaluminum compounds, especially trimethylaluminum, and alumoxanes.

A persistent problem of the foregoing processes is the ability to produce the intermediate diamide complex in high yield and purity. Because the initial exchange step is an equilibrium process, complete conversion generally cannot be attained even after resorting to the use of elevated temperatures and/or venting or vacuum removal of amine byproducts. A process in which complexation of the metal by a ligand is facilitated, thereby resulting in the use of lower reaction temperatures, shorter reaction times, and/or characterized by higher yields, is still desired. In addition, a process in which the multiple steps of the prior art are combined in a single unified or "one-pot" process is desired as well.

SUMMARY OF THE INVENTION

In accordance with this invention there is provided an improved process for the preparation of Group 4 metal hydrocarbyl complexes the steps of the process comprising contacting a Group 4 metal amide with a neutral source of a monovalent or divalent, Lewis base ligand group and a Lewis acid hydrocarbylating agent under conditions to form a Group 4 metal hydrocarbyl complex.

The products are highly valuable for use as catalysts in combination with activating cocatalysts such as alumoxanes or cation forming agents in the polymerization of olefins to high molecular weight polymers.

DETAILED DESCRIPTION OF THE INVENTION

All references to the Periodic Table of the Elements herein shall refer to the Periodic Table of the Elements, published and copyrighted by CRC Press, Inc., 1999. Also, any references to a Group or Groups shall be to the Groups or Groups reflected in this Periodic Table of the Elements using the IUPAC system for numbering groups. For purposes of United States patent practice, the contents of any patent, patent application or publication referenced herein are hereby incorporated by reference in their entirety, especially with respect to the disclosure of synthetic techniques and general knowledge in the art. The term "comprising" when used herein with respect to a composition, mixture or process is not intended to exclude the additional presence of any other compound, component or step.

Suitable Group 4 metal amides for use in the present invention correspond to the formula, $M(NR_2)_m X_n$, wherein M is a Group 4 metal, especially hafnium;

R independently in each occurrence is a $C_{1-20}$ hydrocarbyl group, a $C_{1-20}$ halohydrocarbyl group, or two R groups are joined together thereby forming a divalent derivative;

X is an anionic ligand of up to 20 atoms not counting hydrogen or two X groups are joined together thereby forming a divalent derivative, preferably each X group is hydride, halide, or a hydrocarbyl-, silyl-, hydrocarbyloxy- or siloxy-group of up to 10 atoms; most preferably chloride or methyl;

m is an integer from 1 to 4 and n is an integer equal to 4−m.

Preferred Group 4 metal amides are Group 4 metal tetrakis(N,N-dihydrocarbyl)-amides, especially Group 4 metal tetrakis(N,N-dimethyl)amides, most especially hafnium tetrakis(N,N-dimethyl)amide.

The foregoing Group 4 metal amides are contacted with a neutral source of the desired Lewis base ligating species thereby generating free amine. Suitable ligand sources are monovalent and divalent compounds of the formula L-H or H-L-H wherein L is a monovalent or divalent Lewis base ligand, in which case the resulting free amine corresponds to the formula $NHR_2$. Examples of suitable sources of Lewis base ligating species include aliphatic and aromatic diamine compounds, and hydrocarbylamine substituted aromatic heterocyclic compounds.

In particular, suitable sources of Lewis base ligating species include the difunctional Lewis base compounds disclosed in WO 02/38628, especially hydrocarbylamine substituted heteroaryl compounds of the formula $R^1HN$-$T$-$R^2$ (I), wherein $R^1$ is selected from alkyl, cycloalkyl, heteroalkyl, cycloheteroalkyl, aryl, and inertly substituted derivatives thereof containing from 1 to 30 atoms not counting hydrogen;

T is a divalent bridging group of from 1 to 20 atoms other than hydrogen, preferably a mono- or di-$C_{1-20}$ hydrocarbyl substituted methylene or silane group, and $R^2$ is a $C_{6-20}$ heteroaryl group, especially a pyridin-2-yl- or substituted pyridin-2-yl group.

Preferred examples of the foregoing difunctional Lewis base compounds correspond to the formula:

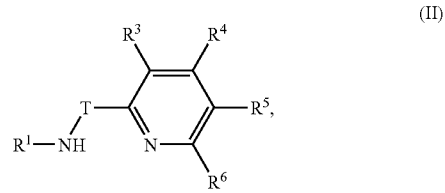

wherein $R^1$ and T are as previously defined, and $R^3$, $R^4$, $R^5$ and $R^6$ are hydrogen, halo, or an alkyl, cycloalkyl, heteroalkyl, heterocycloalkyl, aryl, or silyl group of up to 20 atoms not counting hydrogen, or adjacent $R^3$, $R^4$, $R^5$ or $R^6$ groups may be joined together thereby forming fused ring derivatives.

Highly preferred examples of the foregoing difunctional Lewis base compounds correspond to the formula:

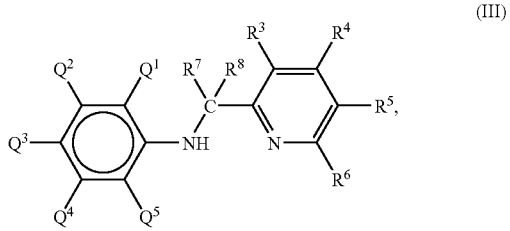

(III)

wherein $R^3$, $R^4$, $R^5$ and $R^6$ are as previously defined, preferably $R^3$, $R^4$, and $R^5$ are hydrogen, or $C_{1-4}$ alkyl, and $R^6$ is $C_{6-20}$ aryl, most preferably naphthyl;

$Q^1$, $Q^2$, $Q^3$, $Q^4$, and $Q^5$ are independently each occurrence hydrogen or $C_{1-4}$ alkyl, most preferably $Q^1$ and $Q^5$ are isopropyl and $Q^2$, $Q^3$ and $Q^4$ are hydrogen; and $R^7$ and $R^8$ independently each occurrence are hydrogen or a $C_{1-20}$ alkyl or aryl group, most preferably one of $R^7$ and $R^8$ is hydrogen and the other is a $C_{6-20}$ aryl group, especially a fused polycyclic aryl group, most preferably an anthracenyl group.

The most highly preferred difunctional Lewis base compound for use herein corresponds to the formula:

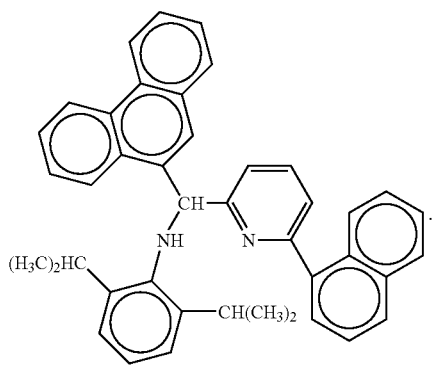

(IV)

Under the reaction conditions of the present invention, it has been discovered that the hydrogen of the 2-position of the naphthyl group substituted at the 6-position of the pyridinyl group is subject to elimination, thereby uniquely forming metal complexes wherein the metal is covalently bonded to both the resulting internal amide group and to the 2-position of the naphthyl group, as well as stabilized by coordination to the pyridinyl nitrogen atom through the electron pair thereof. Accordingly, preferred metal complexes contain a difunctional Lewis base ligand additionally coordinated to the metal by means of an electron pair.

The foregoing reaction is performed in the presence of a Lewis acid hydrocarbylating agent, preferably a tri($C_{1-10}$ hydrocarbyl)aluminum compound, a tri($C_{1-10}$ hydrocarbyl)boron compound, or a halogenated derivative thereof, more preferably, a tri($C_{1-4}$ alkyl)aluminum compound, most preferably trimethylaluminum. Such reagent uniquely promotes amine elimination by acting as an acceptor therefor but simultaneously, supplies additional hydrocarbyl or substituted hydrocarbyl ligands to the replacement reaction. As a result, not only are amide groups removed and replaced by -L or -L-ligands, but additional remaining amide groups, preferably all remaining amide groups are replaced by hydrocarbyl ligands, thereby forming the desired metal hydrocarbyl complex in one process. In a highly desired embodiment of the process a stoichiometric excess of hydrocarbylating agent, preferably trimethylaluminum is used in order to both sequester amine groups eliminated by the exchange reaction, thereby promoting complex formation, and alkylate the resulting metal complex. Accordingly, the Group 4 metal amide and Lewis base compounds are employed in about stoichiometric amounts, preferably in molar ratios (based on amide compound to Lewis base compound) from 1:2 to 2:1. The quantity of Lewis acid compound used is preferably from 2:1 to 10:1, more preferably from 4:1 to 6:1 based on Group 4 metal amide compound.

As an illustration, starting from hafnium tetrakis(dimethylamide) and excess trimethylaluminum the resulting metal complex prepared according to the present invention is in high yield and efficiency is:

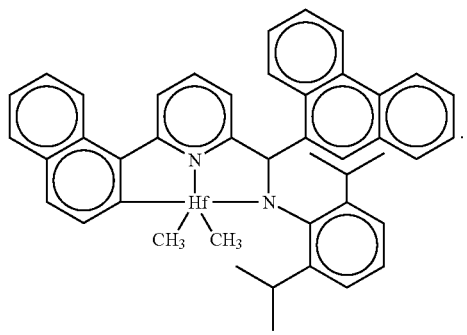

The amide elimination and hydrocarylation conditions used in the present process include moderate temperatures from 0 to 100° C., especially from 25 to 75° C., reduced, atmospheric or elevated pressures from 0 to 100 kPa, preferably atmospheric pressure, times from 1 minute to 10 days, preferably from 10 minutes to 2 hours, and use of an aliphatic or aromatic solvent, preferably toluene or ethylbenzene. The resulting complexes may be recovered by filtration, extraction, precipitation, or other suitable technique.

The resulting Group 4 metal complexes are activated to form the actual catalyst composition by combination with a cocatalyst, preferably an aluminoxane, a cation forming cocatalyst, or a combination thereof and desirably employed to polymerize olefins or combinations of olefins, especially ethylene, propylene, 1-butene, 1-hexene, 1-octene; mixtures thereof; mixtures of the foregoing monomers with vinylaromatic monomers or conjugated or non-conjugated dienes; and mixtures of all of the foregoing monomers. The process is characterized by low temperatures and pressures, typically from 25 to 50° C. and pressures from atmospheric to 10 MPa.

Suitable alumoxanes for use herein include polymeric or oligomeric alumoxanes, especially methylalumoxane, triisobutyl aluminum modified methylalumoxane, or isobutylalumoxane; neutral Lewis acid modified polymeric or oligomeric alumoxanes, such as the foregoing alkylalumoxanes modified by addition of a $C_{1-30}$ hydrocarbyl substituted Group 13 compound, especially a tri(hydrocarbyl)aluminum- or tri(hydrocarbyl)boron compound, or a halogenated (including perhalogenated) derivative thereof, having from 1 to 10 carbons in each hydrocarbyl or halogenated hydrocarbyl group, more especially a perfluorinated tri(aryl)boron compound or a perfluorinated tri(aryl)aluminum compound.

The Group 4 metal complexes may also be rendered catalytically active by combination with a cation forming cocatalyst, such as those previously known in the art for use with Group 4 metal olefin polymerization complexes. Suitable cation forming cocatalysts for use herein include neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium-, lead- or silver salts of compatible, noncoordinating anions; and combinations of the foregoing cation forming cocatalysts and techniques. The foregoing activating cocatalysts and activating techniques have been previously taught with respect to different metal complexes for olefin polymerizations in the following references: EP-A-277,003, U.S. Pat. Nos. 5,153,157, 5,064,802, 5,321,106, 5,721,185, 5,350,723 5,425,872, 5,625,087, 5,883,204, 5,919,983, 5,783,512, WO 99/15534, WO99/42467, (equivalent to U.S. Ser. No. 09/251,664, filed Feb. 17, 1999).

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. The term "overnight", if used, refers to a time of approximately 16–18 hours, the term "room temperature", refers to a temperature of about 20–25° C., and the term "mixed alkanes" refers to a commercially obtained mixture of $C_{6-9}$ aliphatic hydrocarbons available under the trade designation Isopar E®, from Exxon Chemicals Inc. In the event the name of a compound herein does not conform to the structural representation thereof, the structural representation shall control. The synthesis of all metal complexes and the preparation of all screening experiments were carried out in a dry nitrogen atmosphere using dry box techniques. All solvents used were HPLC grade and were dried and deoxygenated before their use.

Example 1

A metal complex was prepared according to the following reaction scheme:

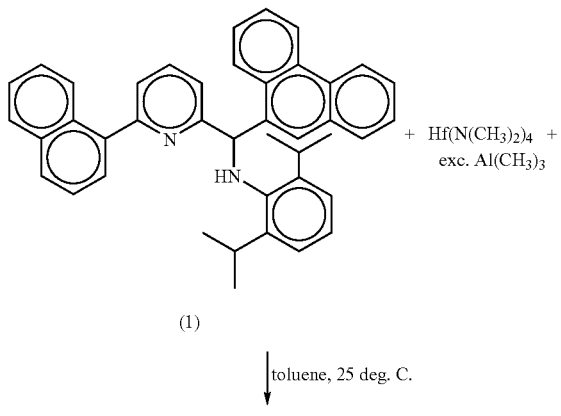
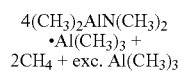
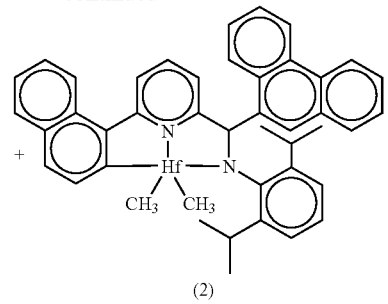

To a 50 mL Parr reactor equipped with a stirrer in a glovebox at room temperature was added 20 ml of toluene and 500 mg (0.88 mmol) of (1). Hafnium tetrakis(dimethylamide) (342 mg, 0.96 mmol) was added. After 20 minutes 7.9 ml of a 2.0 M solution of trimethylaluminum in hexane (15.8 mmol) was added. After stirring for 3 days the solution was passed through a pad of calcined silica. The silica was rinsed with small amounts of toluene. The product was subjected to drying under dynamic vacuum. Then the solid residue was stirred in 20 ml of pentane, recovered by filtration and dried under dynamic vacuum. The desired dimethyl hafnium complex was recovered as a yellow solid.

Catalytic activity was confirmed by polymerization of 450 g of propylene monomer in 500 ml hexane in a 2 L polymerization reactor at 90° C. using 1.0 μmole of catalyst and a hexane solution of methyldi(octadecylammonium) tetrakis(pentafluorophenyl)borate cocatalyst in 1:1 B:Hf molar ratio.

The invention claimed is:
1. A process for the preparation of a Group 4 metal hydrocarbyl complex comprising a monovalent or divalent Lewis base ligand the steps of the process comprising contacting a Group 4 metal amide with a neutral source of a monovalent or divalent, Lewis base ligand group and a Lewis acid hydrocarbylating agent under conditions to form the Group 4 metal hydrocarbyl complex.
2. The process of claim 1 wherein the Group 4 metal amide corresponds to the formula, $M(NR_2)_m X_n$,
wherein M is a Group 4 metal;
R independently in each occurrence is a $C_{1-20}$ hydrocarbyl group, a $C_{1-20}$ halohydrocarbyl group, or two R groups are joined together thereby forming a divalent derivative;
X is an anionic ligand of up to 20 atoms not counting hydrogen or two X groups are joined together thereby forming a divalent derivative;
m is an integer from 1 to 4; and
n is an integer equal to 4−m.
3. A process according to claim 2 wherein each X group is hydride, halide, or a hydrocarbyl-, silyl-, hydrocarbyloxy- or siloxy-group of up to 10 atoms.
4. A process according to claim 3 wherein each X is chloride or methyl.
5. A process according to any one of claims 1–4 wherein M is hafnium.
6. A process according to any one of claims 1–4 wherein the Group 4 metal amide is a Group 4 metal tetrakis(N,N-dihydrocarbyl)amide.

7. A process according to claim 6 wherein the Group 4 metal amide is a Group 4 metal tetrakis(N,N-dimethyl)amide.

8. A process according to claim 7 the Group 4 metal amide is hafnium tetrakis(N,N-dimethyl)amide.

9. A process according to any one of claims 1–4 wherein the neutral source of a monovalent or divalent, Lewis base ligand group is:

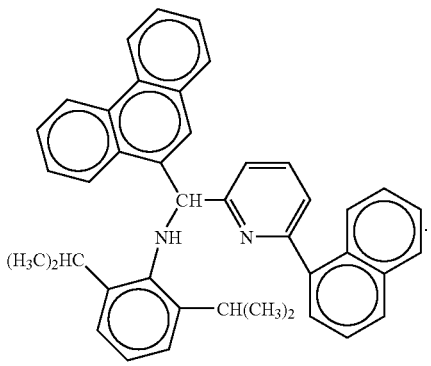

10. A process according to claim 5 wherein the neutral source of a monovalent or divalent, Lewis base ligand group is:

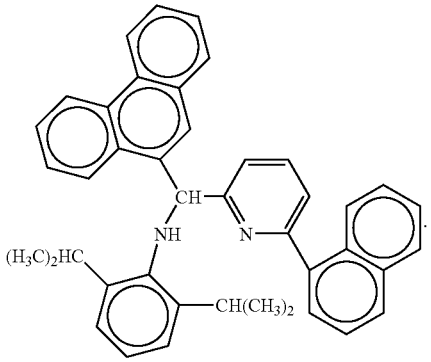

11. A process according to any one of claims 1–4 wherein the Lewis acid hydrocarbylating agent is employed in excess based on quantity of Group 4 metal amide.

12. A process according to claim 11 wherein the Lewis acid hydrocarbylating agent is trimethylaluminum.

13. A process according to claim 5 wherein the Lewis acid hydrocarbylating agent is employed in excess based on quantity of Group 4 metal amide.

14. A process according to claim 13 wherein the Lewis acid hydrocarbylating agent is trimethylaluminum.

* * * * *